(12) United States Patent
Simm et al.

(10) Patent No.: US 8,177,063 B1
(45) Date of Patent: May 15, 2012

(54) HYPODERMIC NEEDLE HOLDER

(75) Inventors: Kendell Simm, Fountain Valley, CA (US); Dale Emis, Irvine, CA (US)

(73) Assignee: Kendell A. Simm, Fountain Valley, CA (US)

( * ) Notice: Subject to any disclaimer, the term of this patent is extended or adjusted under 35 U.S.C. 154(b) by 0 days.

(21) Appl. No.: 12/930,237

(22) Filed: Dec. 29, 2010

(51) Int. Cl.
*B65D 83/10* (2006.01)
*A61M 5/00* (2006.01)

(52) U.S. Cl. .................................. 206/366; 604/110

(58) Field of Classification Search ............... 206/365, 206/366, 370; 604/110, 192, 263
See application file for complete search history.

(56) References Cited

U.S. PATENT DOCUMENTS

| | | | |
|---|---|---|---|
| 75,689 A | 3/1868 | Mattson | |
| 1,625,035 A | 4/1927 | Lilly | |
| 2,523,877 A | 9/1950 | Pestoli | |
| 3,133,635 A | 5/1964 | Gordon et al. | |
| 3,727,749 A | 4/1973 | Martin | |
| 3,746,155 A | 7/1973 | Seeley | |
| 3,937,219 A | 2/1976 | Karakashian | |
| 4,351,434 A | 9/1982 | Elisha | |
| 4,375,849 A | 3/1983 | Hanifi | |
| 4,452,358 A | 6/1984 | Simpson | |
| 4,520,926 A | 6/1985 | Nelson | |
| 4,758,230 A | 7/1988 | Rycroft | |
| 4,802,579 A | 2/1989 | Hall et al. | |
| 4,878,897 A * | 11/1989 | Katzin | 604/192 |
| 4,892,191 A | 1/1990 | Nakamura | |
| 4,917,243 A | 4/1990 | Abrams | |
| 4,919,264 A | 4/1990 | Shinall | |
| 4,984,686 A | 1/1991 | Shillington | |
| 4,995,871 A | 2/1991 | Sasaki | |
| 5,024,326 A | 6/1991 | Sandel et al. | |
| 5,037,400 A * | 8/1991 | Curry | 604/192 |
| 5,046,612 A | 9/1991 | Mostarda | |
| 5,133,454 A | 7/1992 | Hammer | |
| 5,265,724 A | 11/1993 | Dondlinger | |
| 5,334,151 A | 8/1994 | Santilli | |
| 5,385,556 A * | 1/1995 | Wang et al. | 604/192 |
| 5,409,112 A | 4/1995 | Sagstetter | |
| 5,482,067 A | 1/1996 | Wittrock et al. | |
| 5,484,403 A | 1/1996 | Yoakum | |
| 5,492,671 A | 2/1996 | Krafft | |
| 5,566,828 A | 10/1996 | Claes et al. | |
| 5,573,113 A | 11/1996 | Shillington | |
| 5,673,790 A * | 10/1997 | Schramm | 206/366 |
| D401,690 S | 11/1998 | Simm | |
| 5,850,917 A | 12/1998 | Denton et al. | |
| 6,279,743 B1 | 8/2001 | Ballard et al. | |
| 6,783,003 B2 * | 8/2004 | Simm et al. | 206/366 |

* cited by examiner

*Primary Examiner* — Bryon Gehman
(74) *Attorney, Agent, or Firm* — Curtis L. Harrington; Harrington & Harrington

(57) ABSTRACT

A combination needle holder and suture needle and suture thread device has a variety of features that make it an optimal device for safe storage and disposal of hypodermic needles and disposal of sutures. The needle holder of the present invention includes at least one hypodermic needle retainer for engaging and keeping a hypodermic needle in a variety of settings. A flange with adhesive assist helps position the holder in a wide variety of instances of different structures being available to the practitioner.

20 Claims, 9 Drawing Sheets

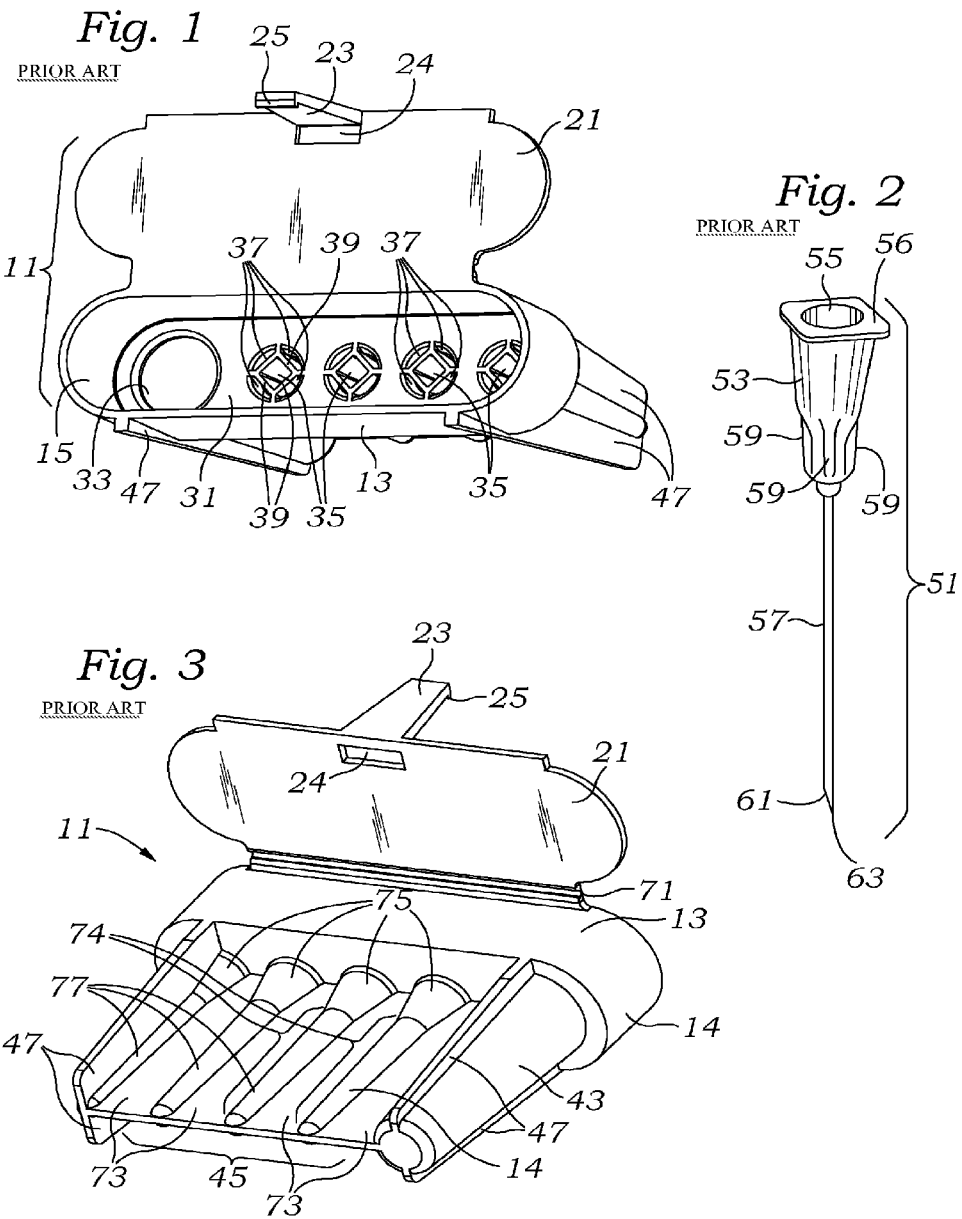

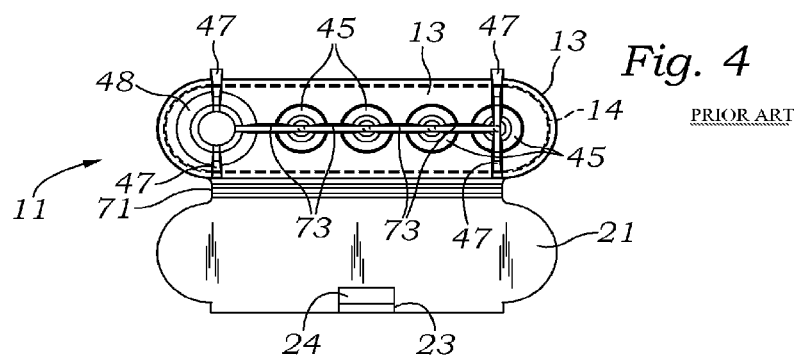
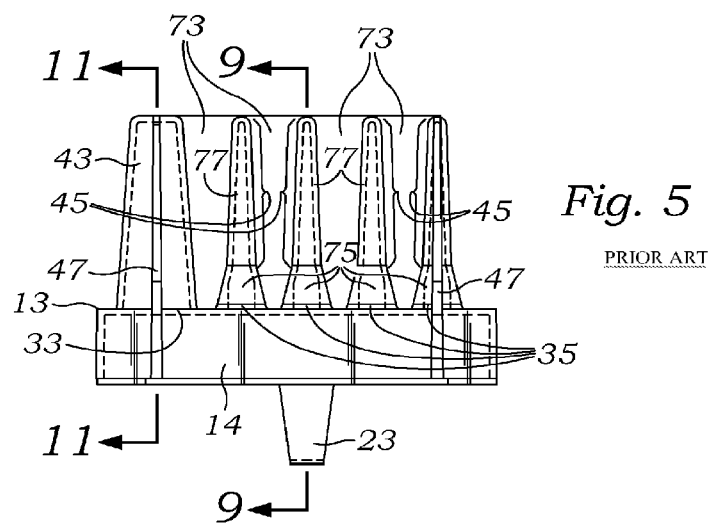
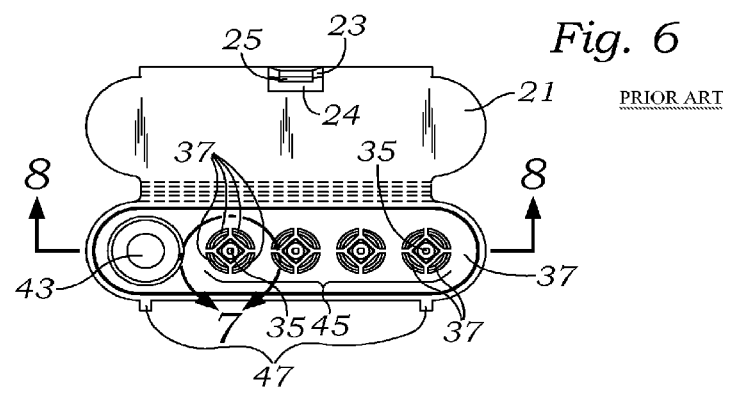

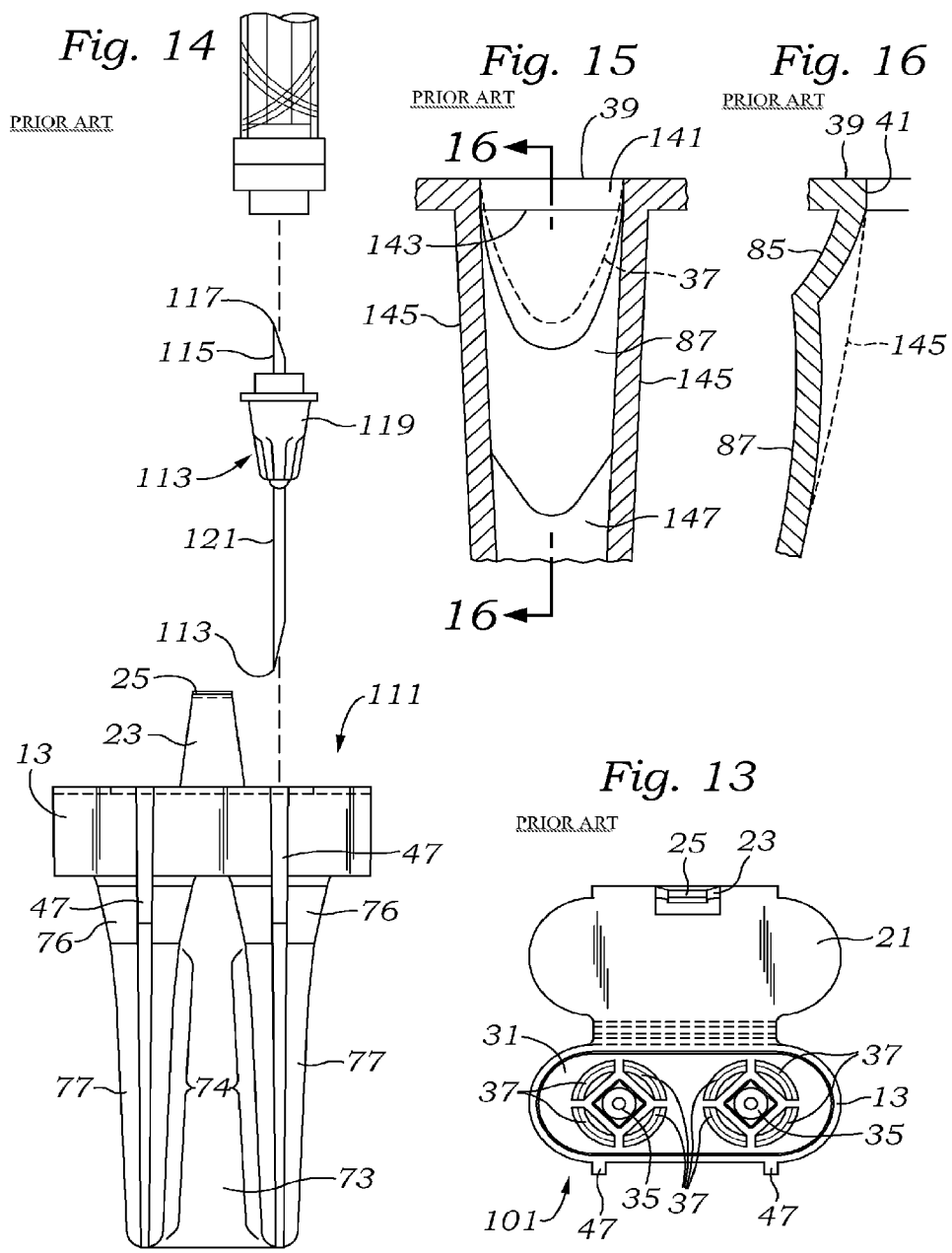

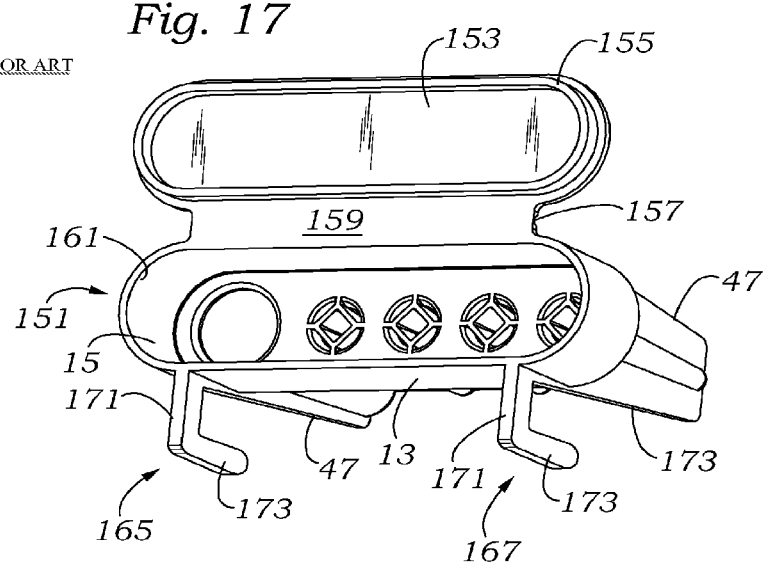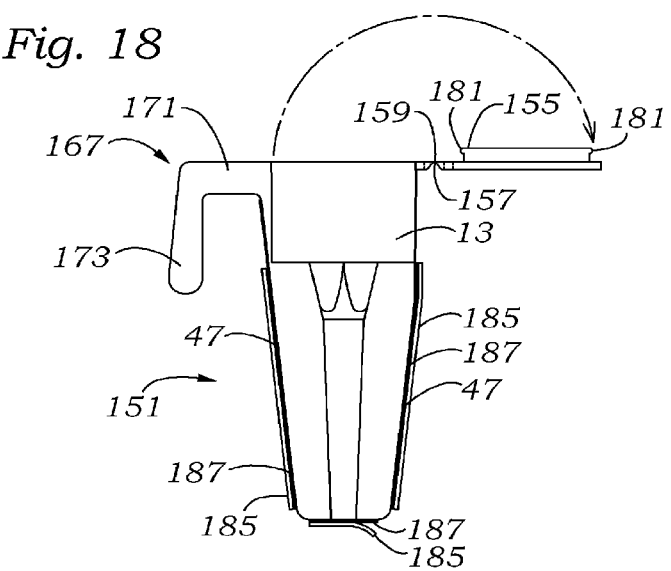

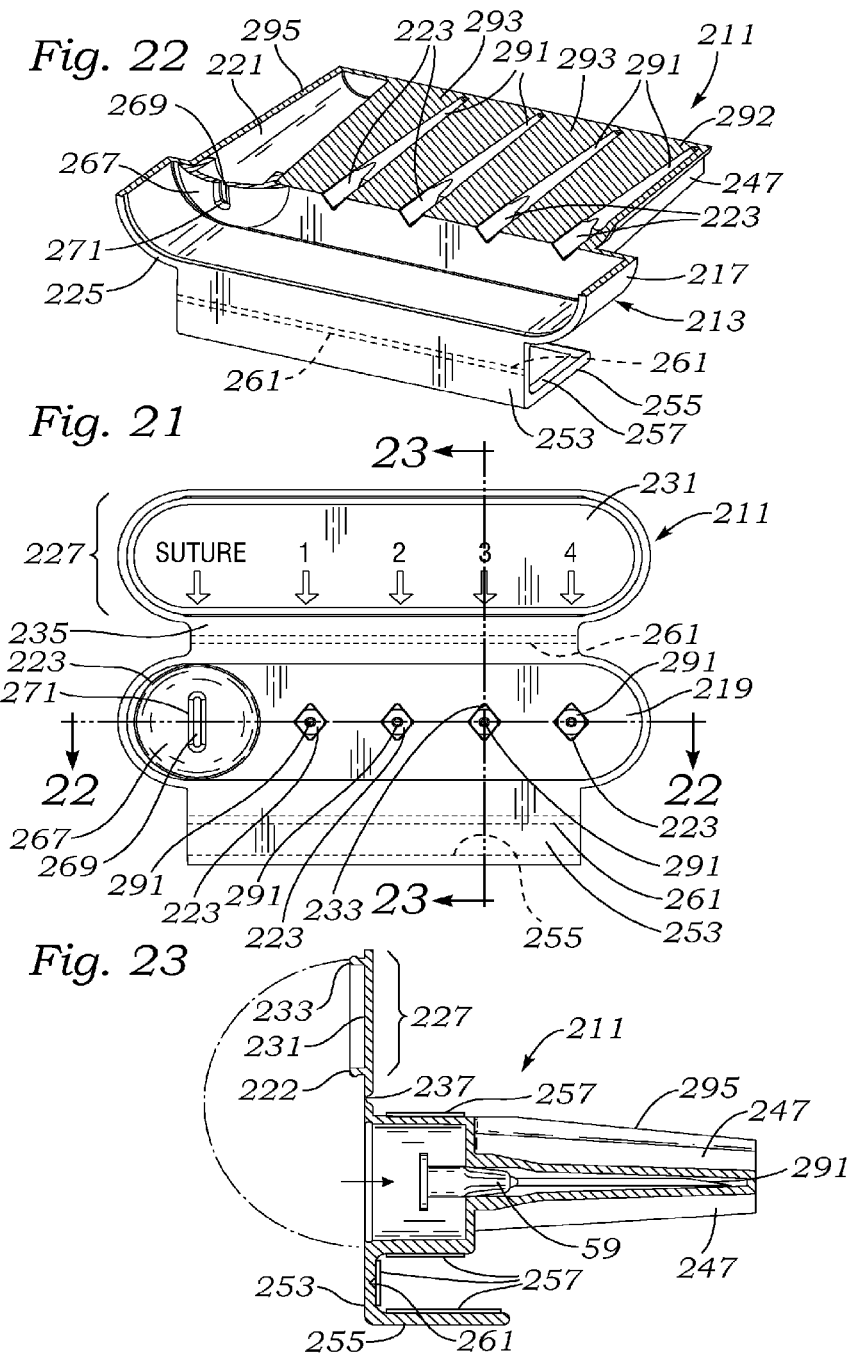

HYPODERMIC NEEDLE HOLDER

FIELD OF THE INVENTION

The present invention relates to hypodermic needle holders, suture needle disposal and disposal structures, and more specifically to a hypodermic needle holder and disposal structure that minimizes the risk of inadvertent needle sticks that may result from coupling or uncoupling a hypodermic needle from a hypodermic syringe or recapping a hypodermic needle, or may result from improper storage of a hypodermic needle while the needle is temporarily not in use, as well as a suture disposal compartment secured by a cap having an abbreviated slot opening, a continuous flange with an in-plate hinge depression and an adhesive attachment provided on the flange.

BACKGROUND OF THE INVENTION

Use and handling of hypodermic needles is a frequent occurrence in the field of medicine. Hypodermic needle systems typically consist of a hypodermic syringe that is quickly and easily removably attachable to a variety of hypodermic needle types and sizes by frictional engagement or by screw-on engagement, the latter of which is usually achieved using a LUERLOCK system. Handling and use of hypodermic needles inherently includes a certain amount of risk of accidental needle stick either to the person who may be administering an injection or to others in the immediate vicinity if a used hypodermic needle is improperly stored or carelessly placed prior to disposal.

Recapping a hypodermic needle after an injection is a likely cause of a large percentage of the composite risk factor for needle sticks in health care settings; most institutions discourage recapping of hypodermic needles under any circumstances. In some states and counties, safety laws prohibit recapping and other unsafe disposal practices. Unfortunately, this may also mean that the person responsible for disposing of a used hypodermic needle and syringe may have to travel more than a short distance to reach a sharps disposal container, thereby exposing more people than necessary to the potential hazard of incurring a needle stick and increasing their own risk for injury en route.

In some procedures, and for a given patient, there arises the need to re-use a needle during the procedure. For dentists who apply numbing medication in the oral cavity, repeated applications may be required with corresponding re-use of the needle. In other re-anesthetizing uses, such as during suturing, a needle may be re-used. For example, where the tissue requires further, later in time handling of the syringe and needle to either continue anaesthetization or to move on to another area on the patient's body. In these and many other re-use scenarios, there is simply no proper procedure for interim protection of personnel, isolation of the used and to be used again needle. In some hospitals it is required that a drape cover the sterile field when significant time elapses between a procedure and the next procedure, or where when significant time elapses between a series of procedures. The use of a drape can pick up contamination and spread it with subsequent manipulation of the drape. The drape may catch on the needle or other objects in the sterile field and produce a stick through the drape or even catch the needle and cause it to drop to the floor when the drape is removed. Although the use of the drape to block dust and airborne contaminants, the increased risk of sticks, cuts and upset spills of the materials in the field increase several fold when the drape covers the objects in the field, and there is further increase of accident each time the drape is handled after its initial deployment.

Even systems which are touted to be "needle-less" continue to create a danger of needle stick. One recent system includes a seventeen gauge tube with a generally blunt (transverse even tubular end) end which is supposed to be protected by a sleeve. If anything, this system is just as apt to create accidental stick contamination as the needle end is hidden until it makes contact with the skin, and the temporary hiding of the needle in the sleeve causes unwarranted reliance on the sleeve with increased carelessness.

Further, in health care settings, certain intravenous medications are required to be given in incremented doses and are repeated until a desired effect is achieved. When this is the case, it is not uncommon to repeatedly fill the same hypodermic syringe with medication and to perform repeated intravenous injections into a port that leads directly to a vein or leads into an intravenous fluid line that terminates in a vein. This is usually the case, for example, with patients who have problems of an emergent nature, such as cardiac or respiratory arrest, or problems of an urgent nature such as heart failure or respiratory difficulty, or even for patients undergoing surgery. Because large volumes of fluid may be drawn up into a hypodermic syringe in anticipation of needing them, they are often drawn up using a large gauge hypodermic needle, such as an 18 or even a 16 gauge hypodermic needle for speed and convenience, and this may include the above "needle-less" system. Injecting an intravenous port with such a large gauge hypodermic needle even once could damage the membrane of the port, causing leakage at the port, and thus rendering the entire intravenous tubing useless such that it would have to be replaced. For this reason, administration of intravenous medications typically takes place using a smaller gauge hypodermic needle, usually less than a 20 gauge. This may require that the large gauge needle and the small gauge needle be intermittently exchanged for one another, and certainly requires that whichever needle is not in use be kept from contamination. In dire circumstances, where the patient's condition may be serious and where the environment is likely to be somewhat chaotic as a result, the chances of improper placement of a used hypodermic needle increases significantly. Subsequently, the risk of hypodermic needle contamination increases, as does the risk for inadvertent needle stick for personnel who are caring for the patient, and even for family members or others who may be present.

In caring for a patient who receives frequent injections of any kind at the bedside, health care personnel may have their attention diverted from the task at hand by some distraction, and may subsequently place a used hypodermic needle on a bedside table or even on the bed beside the patient in order to address the distraction. Not only could this practice cause unintentional injury to the patient, but health care personnel and others who may have occasion to enter a patient's room after the fact are also at risk of being stuck or otherwise injured by the stray hypodermic needle.

Yet another potentially harmful procedure is that of drawing up medications from a vial that requires puncture of a membrane in order to access the medication within the vial. Although the hypodermic needle is not biologically contaminated, this practice still presents the potential for injury to the health care worker or others, since it requires recapping the hypodermic needle until the medication is to be administered. Similarly, medications contained in scored glass vials that require breakage of the vial and drawing up of the medication through a hypodermic needle is another practice that increases risk of needle stick, primarily because of the need for recapping the hypodermic needle prior to giving the injection.

A carelessly placed hypodermic needle that causes injury may result in temporary incapacitation of the health care team member who sustains the injury. Prompt treatment of the injury is encouraged by most institutions, and incident reports are mandatory, thereby potentially compromising patient well-being by decreasing the number of staff available for immediate patient care.

Yet another potentially injurious situation is that involving hypodermic needle disposal. Disposing of an uncapped hypodermic needle, even into a designated sharps container, can be a dangerous act in itself. Because of the design of most sharps containers, if the container is nearly full, it can prove to be difficult if not impossible to safely insert an exposed hypodermic needle into the box without injury either from the hypodermic needle being inserted or from other needles that may have become lodged in the opening of the box.

While hypodermic needles and syringes are likely the cause of most needle stick injuries, surgical needles and other small sharps containers commonly used in a health care setting are also potential hazards if not disposed of properly. Because suture needles are quite small, simple suturing at a patient's bedside may result in misplacement of the small suture needle and attached thread should it not be immediately disposed of or placed in a safe location prior to its disposal. A stray needle in the patient's bed or on the floor could result in patient injury or injury to health care workers, patient family, or others who may come in contact with the patient or who may have occasion to be in the patient's room. Lack of an appropriate disposal container in an operating room could also lead to misplacement of suture needles during a patient's surgery; this could be particularly problematic, and could place the patient in unnecessary danger by delaying the completion of the surgery until all suture needles are located.

Other persons at risk for injury from needle stick include family members or unskilled lay persons who may help to care for patients in a home setting and who may regularly assist, for example, with subcutaneous administration of medications such as insulin. Other persons at risk include paramedics and emergency health workers who are always on the move, continually working in harried, difficult conditions and have no prepared surgical field to use as a base of operations. With paramedics, for example, time is of the essence. If too much time is required in either disposing of or temporarily storing a needle, the paramedic may toss it on the ground where it may contaminate others or toss it in the medical kit. Without a proper, inviting and very available place to both store needles during extended procedures and to at least safely and temporarily dispose of needles on the move, needle sticks and the like will remain a major problem to emergency health professionals.

Yet another situation where accidental needle sticks or other injury can occur is after an intravenous line is initiated on a patient. Because the intravenous catheters used are catheter-over-the needle systems, once the catheter is in place, the needle is extracted and disposed of. Whether the intravenous line is started in an emergency situation that may be chaotic, or whether started in the most optimal of situations, the needle may be improperly placed on whatever surface is nearest at hand so that the catheter may be secured and fluids or medication may be administered. Should the needle be forgotten once the procedure is complete, it will pose a risk for those in the immediate vicinity. Some new catheter systems include safety devices, but use of such devices still involves the needle being left out with continued danger of needle sticks at the point.

Although most, if not all, health care institutions have designated procedures for the proper use and disposal of needles, and although most institutions additionally require health care workers to attend continuing education classes for learning safe handling and disposal of sharps and other biologically contaminated equipment, accidental needle sticks continue to occur and are an ongoing problem. The risk of accidental needle stick is cause for serious concern, both to health care workers and to others who may be exposed to the use of hypodermic syringes and needles of any kind, due to the existence and transmissibility of life threatening blood-borne diseases such as hepatitis, and Acquired Immune Deficiency Syndrome (AIDS).

What is therefore needed is a device and method that is easy and convenient to use and that will minimize the risk associated with handling and disposal of hypodermic needles and hypodermic syringes. The proposed device should be useable by trained health care personnel, as well as by unskilled lay persons such as patients, family members, and other care givers. The proposed device should be able to accommodate a variety of sharps or similarly small biologically contaminated items that would be ill disposed of in an ordinary trash can.

Numerous attempts have been made in the prior art to design a safe disposal container for hypodermic syringes and needles. However, such devices do not allow for both the removal and attachment of hypodermic syringes and needles in a safe manner. Such devices also do not teach their sterilization to enable them to be used in any capacity other than their capacity for disposal. All of the prior devices for holding and facilitating safe disposal of the needles will destroy the sterility of the sterile field. Any health care worker walking about with an open container full of contaminated needles should not be allowed anywhere near a sterile field. Many of the devices are not only too contaminated, they are too large for the sterile field. Most of the prior devices which will accommodate large numbers of syringe needles, by being contaminated, require the health care workers to carry the needles to it, again exacerbating the handling problem and increasing danger to others from open carriage of the contaminated material. In prior devices, no attempt is made to either start with a sterile space nor to isolate stored needles from other needles which have been contaminated by other patients.

For example, U.S. Pat. No. 5,046,612 issued to Mostarda et al. and U.S. Pat. No. 4,917,243 issued to Abrams both provide hand held receptacles that extract hypodermic needles from hypodermic syringes. As such the used hypodermic needles are longitudinally placed inside the receptacle and removed from the hypodermic syringe to thereby reduce the risk of injury from the hypodermic needle tip. Both inventions provide different means for inserting the hypodermic needle into the receptacle longitudinally such that the risk of exposure to the sharpened hypodermic needle tip is reduced. However, there are no methods for reusing the hypodermic needle as is necessary when re-filling a hypodermic syringe with fluid or medication or re anesthetizing a patient, or re-injection of a joint.

In U.S. Pat. No. 5,057,656 issued to Galber, a disposal container for hypodermic needles is provided. The container includes a top with suitability shaped openings for the removal of hypodermic needles from hypodermic syringes. Used hypodermic needles are disposed inside the container to protect the health care worker. Also, the needles inserted into the foam filled container can't be reversed and used again as foam fills the needle opening.

Furthermore, in U.S. Pat. No. 4,375,849 issued to Nahifl and U.S. Pat. No. 4,351,434 issued to Elisha, hypodermic needles are disposed in a cylindrical container through an opening in the container top. However, such containers pose a risk of injury to the health care worker because the container is usually held with a hand that can be punctured by the exposed hypodermic needle tip as it is inserted into the container. As such, these containers do not provide a safe method of disposal. Similarly, U.S. Pat. No. 4,995,871 issued to Sasaki et al. And U.S. Pat. No. 4,984,686 issued to Shillington provide enclosure lids that extract the hypodermic needle from the hypodermic syringe and then dispose of the hypodermic needle in an attached container. However, both devices are complex and not easily manufactured and do not provide for the safe storage of exposed hypodermic needle tips.

Additionally, U.S. Pat. No. 4,892,191 issued to Nakamura, discloses a container for the removal and disposal of press or slip type hypodermic needles attached to a hypodermic syringe while U.S. Pat. No. 4,802,579 issued to Hall et al. discloses a container which removes and disposes of hypodermic needles that use screw threads to attach the hypodermic syringe. In both devices, the hypodermic needle is inserted into the disposal container through an opening and engaged thereby. The opening is then used to remove the hypodermic needle from the hypodermic syringe and the exposed hypodermic needle is dropped down into the container. However, neither of these devices provide means for storing the exposed hypodermic needles while being attached or removed from the hypodermic syringe before being disposed.

Furthermore, U.S. Pat. No. 4,191,264 issued to Shinall discloses a removal and disposal device for hypodermic needles. The device comprises individual containers that remove and store the used hypodermic needle in a tacky substance. As such, the device is complicated and expensive to manufacture and does not allow needle re-use. Similarly, U.S. Pat. No. 4,452,358 discloses a box-like device wherein the hypodermic needle is destroyed while being removed from the hypodermic syringe and the container includes multiple compartments and openings for the disposal of other medical instruments such as scalpel blades.

As can be seen from the related prior art, numerous devices have been designed for the disposal of hypodermic syringes and needles. However, none of the prior art devices provide an apparatus that can safely remove, attach and store the hypodermic needle and then properly dispose of the hypodermic needle after use.

What is therefore needed is an inexpensive device that protects the health care worker from inadvertent needle sticks while handling hypodermic needles and syringes. The needed device and method should be simple to use and therefore optimal for use by both trained professional health care workers as well as unskilled lay persons who may have need of using hypodermic syringes and needles in a home care setting. Additionally, there exists a need for provision of both storage of hypodermic needles, with or without a hypodermic syringe attached, and for disposal of hypodermic needles quickly and safely after their use and subsequent detachment from hypodermic syringes. Furthermore, there is a need for containment and disposal of other sharp objects such as suture needles, or other small items that may be biologically contaminated and that would be more appropriately disposed of in a biological waste container rather than in a trash can.

The needed device also should provide a variety of structural aspects which will enable stabilization of such device such that inadvertent shifting or movement of the device will not either cause a loss of a sterile field, or result in contamination from instances where the device is spilled or dropped. Such a device should also preferably contain a structure facilitating disposal of sutures and other small items and permit their entry into a retained disposal area in a manner which will inhibit spillage and escape.

SUMMARY OF THE INVENTION

The needle holder of the present invention has a variety of features that make it an optimal device for safe storage and disposal of hypodermic needles. Further, the needle holder of the present invention is also able to accommodate surgical needles or other small sharps or biologically contaminated articles, and may be easily and conveniently employed in a variety of settings. Alternative embodiments of the present invention will accommodate double-ended hypodermic needles, and larger versions of hypodermic needles such as thoracic, cardiac, or spinal needles.

In the preferred embodiment of the present invention, there is provided a hypodermic needle holder which works with a hypodermic needle having a needle hub adjacent a needle shaft and terminating at a needle tip. The hypodermic needle holder comprises a body portion and a lid portion, the body portion of which defines a compartment having a plurality of needle retainers disposed in a side-by-side relation therein. The needle retainers are sized and configured to frictionally engage the needle hub of a hypodermic needle in a manner wherein the hypodermic needle is fixedly contained within the needle retainer. The needle retainers are frustoconical or conically or of tapering shape and also specially internally shaped for frictional retention of the hypodermic needles. The compartment has a generally rectangular configuration and is optimally formed from a rigid and durable plastic material. The lid portion of the hypodermic needle holder is moveable between an open position where the needle retainers are accessible and a closed position whereat the needle retainers are shielded within the hypodermic needle holder.

The hypodermic needle holder of the present invention also includes a receptacle into which smaller sized needles such as surgical needles may be placed after use. Furthermore, this receptacle may be used for small items such as cotton balls, gauze pads, or discontinued intravenous catheters that may be biologically contaminated and that would be best disposed of in a bio-hazardous waste container, but in a second embodiment where it is covered with a suture cap, only suture and disposal of smaller structures will be possible. The material from which the needle holder may be constructed may be clear in order to facilitate a visual count of suture needles as well as a count of engaged and stored hypodermic needles.

In an alternative embodiment of the present invention, the size of the overall hypodermic needle holder and of the needle retainers themselves are elongated in order to contain longer hypodermic needles such as cardiac, thoracic, or spinal needles.

In yet another alternative embodiment of the present invention, a container is provided with a slightly larger opening in order to accommodate a double ended hypodermic needle such as those used in many dental practices, as well as those used in the medical profession primarily by phlebotomists and in conjunction with devices such as VACUTAINERS.

Further there is provided a method for transferring attachment of a hypodermic needle to or from a hypodermic syringe through the use of a hypodermic needle holder which includes an opening with at least one engaging needle retainer disposed therein. The method includes frictionally engaging the hypodermic needle to the needle retainer both by insertion friction and turning friction. The hypodermic syringe is advanced into the opening of a hypodermic needle holder and subsequently into a needle retainer space and retainer structure for initial axial frictional engagement to cause the hypodermic needle to be frictionally engaged with the retainer structure. The hypodermic syringe can be disengaged from the hypodermic needle by a turning motion against the friction and locking holding power of the needle retainer, to disengage the needle from its LUER fitting. The hypodermic syringe can be re-engaged onto the hypodermic needle by approach of the syringe, and physical engagement of the LUER fitting by a turning motion against the friction and locking holding power of the needle retainer, to re-engage the LUER fitting. Once re-engaged, a simple axial pulling of the syringe and LUER attached needle will disengage the hypodermic needle from the needle retainer. If needed, the hypodermic needle and syringe combination can be disengaged from the needle retainer and removed from the opening of the hypodermic needle holder for further use. By providing a relatively larger structure than a simple cap, movement of the hypodermic needle into and from its storage area is accomplished while the fingers and hand not holding the hypodermic syringe can support the hypodermic needle holder significantly far from the area of entrance of the needle into the hypodermic needle holder. Furthermore, the hypodermic needle holder includes an openable and closable lid portion for selectively accessing the needle retainer wherein the lid portion must be opened prior to advancing the hypodermic syringe into the opening of the hypodermic needle holder.

The present invention further includes a method of removing a hypodermic needle from a hypodermic syringe that includes a hypodermic needle holder having an opening with at least one needle retainer disposed therein. The method comprises advancing a hypodermic syringe with a hypodermic needle coupled thereto into the hypodermic needle holder and subsequently into the needle retainer. Next, the hypodermic needle is frictionally engaged to the needle retainer. The hypodermic syringe is then uncoupled from the hypodermic needle, leaving the hypodermic needle engaged within the needle retainer. The hypodermic syringe and needle may be coupled via a frictional engagement wherein uncoupling the hypodermic syringe from the hypodermic needle comprises pulling the hypodermic syringe away from the hypodermic needle. Alternatively, the hypodermic syringe and needle may be coupled via a LUER fitting such that uncoupling the hypodermic syringe from the hypodermic needle comprises rotation of the hypodermic syringe to disengage the hypodermic needle. Furthermore, the hypodermic needle holder includes a lid portion such that the lid portion must be opened prior to the advancement of the hypodermic syringe into the hypodermic needle holder.

BRIEF DESCRIPTION OF THE DRAWINGS

The invention, its configuration, construction, and operation will be best further described in the following detailed description, taken in conjunction with the accompanying drawings in which:

FIG. 1 is a view of the hypodermic needle holder of the present invention, and illustrates a body portion that defines a compartment having a receptacle at one side and a plurality of needle retainers adjacent the end receptacle, and a lid portion in an open position and with a cantilevered latch connected to the body portion;

FIG. 2 is a perspective expanded view of a hypodermic needle and illustrates a hub adjacent a needle shaft with a beveled edge that terminates at a needle tip.

FIG. 3 is a view of more of the needle support structure of the hypodermic needle holder of FIG. 1 from an elevated perspective and illustrates the overall shape and position of the receptacle and the plurality of needle retainers, and the attachment of the lid portion in an open position with cantilevered latch;

FIG. 4 is a view of the bottom of the hypodermic needle holder of FIGS. 1 and 3 and illustrates the body portion, the extent of the structural support as an "H" overall shape, the position of the receptacle and needle retainers, and the lid portion in an open position;

FIG. 5 is a side view of the hypodermic needle holder of FIGS. 1, 3, and 4 that best illustrates the overall shape and side-by-side orientation of the receptacle and plurality of needle retainers, and clearly illustrates the cantilevered latch extending from the lid;

FIG. 6 is a view of the top of the hypodermic needle holder of FIGS. 1, 3, 4, and 5 and illustrates the body portion, the position of the receptacle and needle retainers, and the lid portion in an open position with single body hinge and cantilevered latch;

FIG. 13 is a top view of a second embodiment of the hypodermic needle holder configured to accommodate a pair of double-ended needles such as dental needles or needles used for phlebotomy;

FIG. 14 is a side view of the second embodiment of the needle holder with an elongated needle accommodation portion utilizable for longer needles, such as cardiac needles, and further illustrating a double-ended needle for illustration purposes;

FIG. 15 is a view taken along section 15-15 of FIG. 7 and illustrating a frontal view of one of side of the four square openings from the top of one of its four flat inner walls and proceeding downwardly into the needle accommodation chamber and particularly illustrating a slanted bib surface which transitions into an inwardly curved surface and which finally transitions to a generally straight angled frusto-conical surface;

FIG. 16 is a side view as seen in FIG. 15 and illustrating the lateral extent of the associated surfaces seen at the same level as seen in FIG. 15;

FIG. 17 is a perspective view of a further embodiment of the hypodermic needle holder having a positive lock lid which is tamper resistant, and having outwardly and downwardly extending projections to independently stabilize the holder;

FIG. 18 is a side view and illustrating further details of the embodiment of FIG. 17 and including a peel strip for attaching the holder to another surface;

FIG. 21 is a plan view looking into the main opening to illustrate the spacing throughout which the planar floor extends;

FIG. 22 is a sectional view taken along line 22-22 of FIG. 21 and illustrating the rectangular to tubular transition for each of the blind bores and illustrating the suture space and its relationship with the suture cap;

FIG. 23 is a sectional view taken along line 23-23 of FIG. 21 and illustrating the rectangular to tubular transition for each of the blind bores and illustrating the suture space and its relationship with the suture cap;

DETAILED DESCRIPTION OF THE PREFERRED EMBODIMENT

Figure 7:
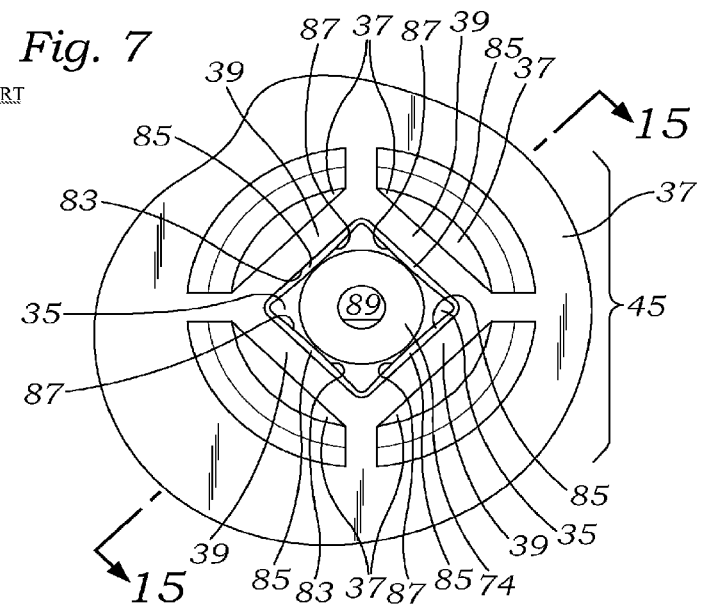
FIG. 7 is an expanded view along line 7 of FIG. 6 that illustrates in more detail the configuration of each of the plurality of needle retainers.

The description and operation of the hypodermic needle holder of the invention will be best described with reference to FIG. 1. The hypodermic needle holder 11 includes a body portion 13 having an upper wall 14 that defines an opening 15. Note that while the overall shape of the opening 15 of the hypodermic needle holder 11 in the preferred embodiment is elongate oval, a variety of shapes is possible without compromise of functionality, such as rectangular, rectangular with curved edges, and the like. The opening 15 is enclosable by a lid portion 21 adjacent the opening 15 of the body portion 13. The lid portion 21 has a cantilever operated latch 23 adjacent a rectangular opening 24 and attached from the lid portion 21. Cantilever operated latch 23 terminates in a right angled extension to form a catch 25. The body portion 13, attached to the lid portion 21 further defines a planar portion 31, within the space beyond the opening 15, having a single circular opening 33 and a series of generally square openings 35, each of the series of square openings 35 are in turn surrounded by a plurality of tapered blind bores 37, separated by a series of four rectangularly placed planar members 39. Each of the series of square openings 35 is arranged in a side-by-side configuration with each of the others in the series of square openings 35, and with respect to the single circular opening 33. This arrangement is not exhaustive of the spatial arrangements possible, but in the preferred embodiment of the hypodermic needle holder 11 it does have a low profile in one dimension to facilitate disposal in a sharps container having a narrow opening. The single circular opening 33 in the planar portion 31 leads into a frustoconical shaped receptacle 43 defined by the body portion 13 of the hypodermic needle holder 11 for containment and eventual disposal of small sharps such as surgical needles, or small biologically contaminated items such as cotton balls, gauze squares, or even discontinued intravenous catheters.

Each of the series of square openings 35 leads into a corresponding one of a plurality of needle retainers 45 defined by the body portion 13 of the hypodermic needle holder 11. The frustoconically shaped receptacle 43 and plurality of needle retainers 45 are arranged such that their longitudinal axes are parallel with one another in order to save space. The axes of the frustoconical receptacle 43 and plurality of needle retainers 45 are arranged generally parallel with the general longitudinal extent of the holder 11. The axes of the frustoconical receptacle 43, and plurality of needle retainers 45 are perpendicular to the planar portion 31.

The hypodermic needle holder 11 may be optimally constructed from a durable but slightly flexible material such as injection molded plastic, that will allow some radially outwardly displacement of each planar member 39 forming each wall of the square of the series of square openings 35 and into the area of each of the plurality of blind bores 37. Any radially outward displacement as a result of inserting a needle (illustrated in FIG. 2) provides an inward grip, in addition to the spatial engagement of the square shape of the planar members on the square aspects of a needle. Construction of the hypodermic needle holder 11 from such a slightly flexible material will thus result in a displacement based inward biasing of the material toward the hub of the needle (illustrated in FIG. 2) for enhancing the frictional engagement and trapping of the needle within the hypodermic needle holder 11. The body portion 13 of the hypodermic needle holder 11 also defines four tapered flanges 47 extending away from the end of the holder 11 adjacent the opening 15, and arranged such that each of two pairs of tapered flanges 47 is disposed at opposite lateral sides of the hypodermic needle holder 11, with one of each pair oppositely disposed from the other of each pair. The tapered flanges 47 help to stabilize the hypodermic needle holder 11 during upright placement on a planar surface such as a table, as well as provide overall structural strength and integrity.

FIG. 2 is a view of a hypodermic needle 51 having a needle hub 53 with opening 55 surrounded by a square flange member 56 to complete a LUER fitting. Between the hub 53 and a needle shaft 57, is a series of four projecting ribs 59 which give the lower part of the hub 53 a square profile to provide a rotational lock with respect to the planar members 39 forming each wall of the square of the series of square openings 35. Each of the projecting ribs 59 will fit at a corner of the junction of each of the planar members 39 to provide a square rotational lock, in addition to the frictional engagement from axial insertion of the hypodermic needle. Needle shaft 57 has a beveled edge 61 that terminates at a needle tip 63.

FIG. 3 is a perspective view of the reverse side of the hypodermic needle holder 11, with respect to the perspective view of FIG. 1 from an elevated perspective and further illustrates the lid portion 21 as having one or more bifurcations 71 adjacent the body portion 13 and extending across the full width of the lid portion 21 at its connection to the body portion 13. The bifurcation 71 may preferably be a thinning of the material in order to direct and control the lid portion 21 to close in a mating relationship over the opening 15. Further, the bifurcation or bifurcations 71 allow a user to manually and orderly open the lid portion 21 in order to gain access to the needle retainers 45 or frustoconical receptacle 43, or to close the lid portion 21 in order to enclose the contents of the frustoconical receptacle 43 and the plurality of needle retainers 45 for safety or for containment of biologically contaminated items.

Ideally, the hypodermic needle holder 11 of the present invention would be constructed of a durable, yet somewhat flexible material such as plastic, to allow for movement of the lid portion 21 without breakage at the bifurcation 71. One material of construction is polypropylene. The bifurcation 71 has sometimes been known as a living hinge, and can be formed by controlling the thickness and width of its extent.

The body portion 13 of the hypodermic needle holder 11 defines an interstitial planar web structure 73 extending between and radially perpendicular to each of the plurality of needle retainers 45 and frustoconical receptacle 43. The interstitial planar web structure 73 as a plane within which the axes of the plurality of needle retainers 45 and frustoconical receptacle 43 reside, thus enhancing the overall structural stability and particularly the upright stability of the hypodermic needle holder 11. FIG. 3 further illustrates that each of the plurality of needle retainers 45 comprises a square opening 35 adjacent a chamber 74 having a tapering or frustoconical first portion 75 adjacent a conical or tapering second portion 77.

FIG. 4 is a view of the bottom of the hypodermic needle holder 11 of FIGS. 1 and 3 and illustrates the lid portion 21 in an open position with attached cantilevered latch 23 and catch 25 (both illustrated in phantom) for securing the lid portion 21 in a closed position. FIG. 4 also illustrates the body portion 13, the frustoconical receptacle 43 and the plurality of needle retainers 45, each in side-by-side orientation with one another. Also illustrated herein are the tapered flanges 47 defined by the body portion 13, and the bifurcation or bifurcations 71 in the lid portion 21 of the hypodermic needle holder that allows for and directs the movement of the lid portion 13 for opening or closing the lid portion 13. FIG. 4 also illustrates the interstitial planar web structure 73 and better details its position in the plane formed by the longitudinal axes of the frustoconical receptacle 43 and plurality of needle retainers 45. FIG. 4 illustrates in phantom format the opening 15 defined by the body portion 13.

FIG. 5 is a side view of the hypodermic needle holder of FIGS. 1, 3, and 4. FIG. 5 illustrates the frustoconical receptacle 43 in side-by-side alignment with the plurality of needle retainers 45, and also clearly illustrates the frustoconical first portion 75 adjacent the tapering second portion 77 of each of the chambers 74. Also illustrated in phantom in FIG. 5 is the opening 15 defined by the wall 14 of the body portion 13 of the hypodermic needle holder 11. The lid portion 21 is illustrated in an open position out of the plane of the page, with cantilevered latch 23 shown and catch 25 illustrated in phantom. The interstitial planar web structure 73 as well as the two of the four tapered flanges 47 is also clearly seen in FIG. 5.

FIG. 6 is a view of the top of the hypodermic needle holder 11 of FIGS. 1, 3, 4, and 5 and illustrates the lid portion 21 in an open position and with attached cantilevered latch 23 and catch 25 for securing the lid portion 21 in a closed position. FIG. 6 illustrates the body portion 13, the opening 15 defined by the body portion 13, the planar portion 31, the single circular opening 33 adjacent the frustoconical receptacle 43, and the series of square openings 35, each surrounded by plurality of blind bores 37, separated from the square openings 35 by series of four rectangularly placed planar members 39 and each of which is adjacent one of the plurality of needle retainers 45. Two of the tapered flanges 47 defined by the body portion 13 are also be seen in FIG. 6. Finally, FIG. 6 illustrates in phantom the bifurcation 71 in the lid portion 21 of the hypodermic needle holder 11 that allows for movement of the lid portion 13. The birfurcation 71 could have been placed on either side of the lid portion 13, or a pair of oppositely located shallow bifurcations could have been placed on opposite sides of the lid portion 13, and the phantom showing is for consistency only. The main idea is some structure which guides folding.

FIG. 7 is an expanded view along line 7 of FIG. 6 and further details the configuration of one of the plurality of needle retainers 45. FIG. 7 illustrates a section of the planar portion 31 having one of the series of square openings 35 surrounded by plurality of blind bores 37 and separated by the series of four rectangularly placed planar members 39. Immediately inside the square opening 35, the needle retainer 45 has four flat inner walls 83 which are immediately adjacent each the series of four rectangularly placed planar members 39. Below the four flat inner walls, a beveled surface angled surface 85 sloping downward into a curve shaped wall 87. The lateral extent of the angled surface 85 has a curved shape which permits the curved shaped wall 87 to lie adjacent the four flat inner walls 83 at the ends of the curved shaped wall adjacent the corners formed by the four flat inner walls 83. The curve shaped wall 87 concentrates the contact area slightly for a more friction laden engagement with the needle hub 53. The chamber 74 has a tapering shape leading to an abbreviated end 89. The angled surface 85 has an adjacent shape as an upwardly open parabolic shape. The beveled surface is a shape consistent with the early extent of a diminishing tapered radius, and finally terminates on the frustoconical first portion 75 of inside of the chamber 74 of the needle retainer 45. Note that the bounds of the convexity of the curve shaped wall 87 define an inwardly curving shape. During use, hypodermic needle 51 is inserted into the square opening 35 and is advanced toward the adjacent frustoconical first portion 75 and subsequent tapering second portion 77 of the chamber 45 so that the ribs 59 begin to place the hypodermic needle 51 in a position where it is limited in turning about its axis. Continued insertion causes the needle hub 53 to contact the curve shaped walls 87 within the frustoconical first portion 75 of the chamber 74. As the needle hub 53 advances into the square opening 35, the needle hub 53 will pass over the four flat inner walls 83, angled surface 85, and the curve shaped wall 87. Once frictional engagement occurs, the four flat inner walls 83 may be slightly outwardly displaced to provide more frictional grasping of the needle hub 53, especially at the middle, innermost aspect of the curve shaped walls 87 below the angled surface 85. While the hypodermic needle 51 is in place with respect to the holder 11, a syringe to which it is attached can be twisted to de-couple the LUER fitting to free the syringe, or the syringe can be brought again to the LUER fitting and twisted to re-couple the syringe to the hypodermic needle 51. Withdrawal of the hypodermic needle 51 from the hypodermic needle holder 11 can then accomplished by a frictional extraction of the hypodermic needle 51 from the needle holder 11.

Figure 8:
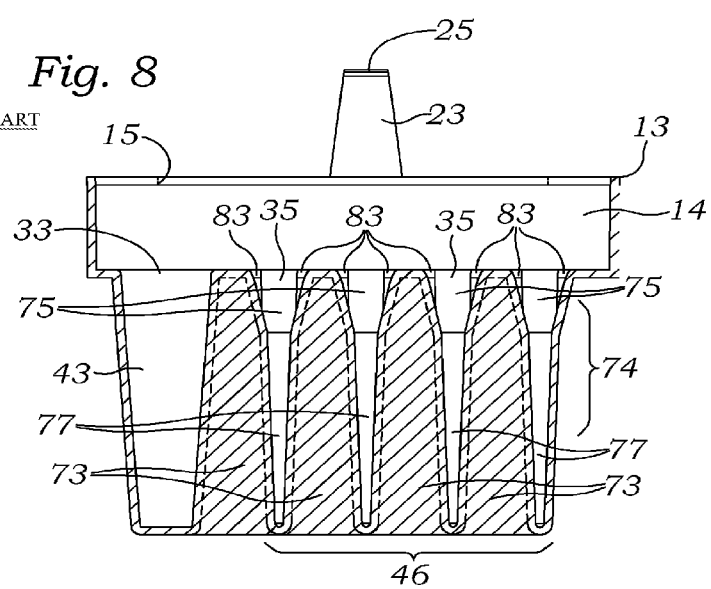
FIG. 8 is a cross-sectional view along line 8-8 of FIG. 6 and more clearly illustrates the body of the hypodermic needle holder and the position of the receptacle and plurality of needle retainers therein.

FIG. 8 is a cross-sectional view of the hypodermic needle holder 11 taken along line 8-8 of FIG. 6 that illustrates the body portion 13, the opening 15 defined by the body portion 13, the cantilevered latch 23 with catch 25, the frustoconical receptacle 43, and the plurality of needle retainers 45. The series of interstitial planar web structure 73 are illustrated as shaded in this figure.

Figure 9:
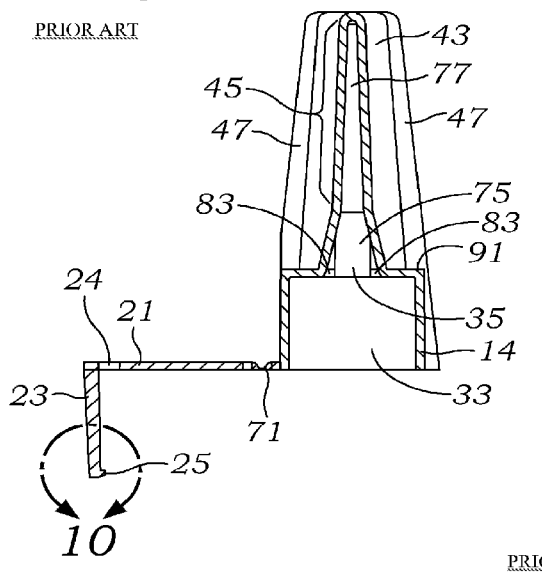
FIG. 9 is a cross-sectional view along line 9-9 of FIG. 5 and more clearly illustrates one of the plurality of needle retainers and its position relative to the body portion, lid portion, and cantilevered latch thereon the lid portion.

FIG. 9 is a cross-sectional view taken along line 9-9 of FIG. 5 that more closely illustrates one of the plurality of needle retainers 45 of the hypodermic needle holder 11. Visible is the body portion 13, two of the tapered flanges 47, the frustoconical receptacle 43, the lid portion 21, the cantilevered latch 23 with catch 25, the bifurcation 71 in the lid portion 21, the opening 15 defined by the body portion 13, and the square opening 35, frustoconical first portion, and conical second portion of the chamber 74. A flat underside surface 91 lies adjacent and just adjacent wall 14. Flat underside surface 91 forms a right angle with respect to the outside of wall 14.

Figure 10:
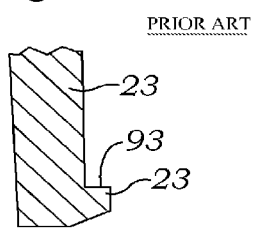
FIG. 10 is an expanded view along line 10 of FIG. 9 that illustrates in detail a catch on the cantilevered latch on the lid portion of the hypodermic needle holder.

FIG. 10 is an expanded view along line 10-10 of FIG. 9 that illustrates in close detail the catch 25 of the cantilevered latch 23 of the hypodermic needle holder 11 extending at a right angle to one side and having a flat portion 93 which will contact and complementarily fit the flat underside surface 91 to enable the lid portion 21 to be locked over the opening 15 to form an enclosure from which any hypodermic needles 51 cannot escape. Typically, the lid portion 21 will be closed and locked at one time, usually just before disposal.

Figure 11:
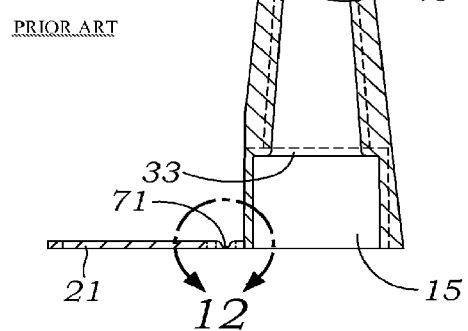
FIG. 11 is a cross-sectional view along line 11-11 of FIG. 5 that more closely illustrates the overall shape of the receptacle and its position relative to the lid portion of the hypodermic needle holder.

FIG. 11 is a cross-sectional view taken along line 11-11 of FIG. 5 that more closely illustrates the frustoconical receptacle 43 and single circular opening 33 of the hypodermic needle holder 11. In FIG. 11, the body portion 13, opening 15 defined thereby, lid portion 21, and bifurcation 71 therein may easily be seen.

Figure 12:
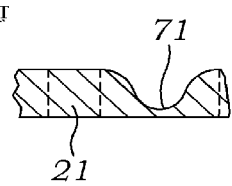
FIG. 12 is an expanded view along line 12 of FIG. 11 that illustrates a bifurcation in the lid portion to allow for movement of the lid portion.

FIG. 12 is an expanded view along line 12-12 of FIG. 11 that more closely details the bifurcation 71 of the lid portion 21. As has been observed, the bifurcation in this case is a thinning of the material and such thinning can occur on either or both sides of the lid portion. Multiple thinned areas can be used in order to control the bending of the material to form a hinge.

FIG. 13 is a top view of a second embodiment of the hypodermic needle holder as a holder 101 configured to accommodate a pair of double-ended needles such as dental needles or needles used in conjunction with VACUTAINERS for phlebotomy. In this embodiment of the hypodermic needle holder 101, the diameters of the series of square openings 35 of the needle retainers 45 are sized larger to accommodate a larger needle hub (illustrated in FIG. 14). This embodiment of the hypodermic needle holder 11 may be utilized anywhere, but may be best suited for health care facilities such as dentist's offices, laboratories, mobile blood banks, and other locations where use of a double-ended hypodermic needle is common.

A further embodiment of the hypodermic needle holder is seen as holder 111 and is seen in FIG. 14. The overall size of the hypodermic needle holder 111 for cardiac and other elongate needles is itself longer. Cantilevered latch 23 and catch 25, the body portion 13, the opening 15 defined thereby, and two of the tapered flanges 47 may also be seen in this figure. Finally, the lid portion 21 is illustrated in phantom in FIG. 14.

FIG. 14 further illustrates, as an example, a double-ended hypodermic needle 113. Double ended hypodermic needle 91 has a first needle shaft 115 terminating in a first needle tip 117 at one end and adjacent a needle hub 119 at an opposite end. The needle hub is adjacent one end of a second needle shaft 121 that is typically longer in length than the first needle shaft 115 and that terminates in a second needle tip 123 at an opposite end. FIG. 14 best illustrates the heightened size of the second embodiment of the hypodermic needle holder 11 to provide for accommodation of a double-ended needle 91 such as the one illustrated herein. In FIG. 14, the proper position of double-ended needle 113 for insertion into the hypodermic needle holder 111 is shown. Note that the hypodermic needle holder 11 may be also be manufactured sized to fit any length of hypodermic needle such as thoracic, cardiac, or spinal needles. The double-ended needle 113 is shown attached to a syringe 131 and is especially preferable to use the syringe 131 for insertion of doubled-ended needles for safety.

The hypodermic needle holder 11 has an unusual shape within its series of square openings 35. The shape is intended to simultaneously (1) provide easy entry with minimum restriction, (2) provide a square engagement, and upon further insertion (3) provide a frictional hold by concentrating force on a relatively limited amount of common structure/material in order to obtain a frictional hold on the hypodermic needle 51.

FIG. 15 is a view taken along section 15-15 of FIG. 7 and illustrating a frontal view of one of side of the four square openings 35 from the top of one of the four rectangularly placed planar members 39. The view taken along section 15-15 is unlike the views taken generally oriented to the hypodermic needle holder 11 since directional normal to the general extent of the holder 11 portray the square openings 35 as diamond shape. It is understood that the openings may be oriented differently, such as where each one of the four rectangularly placed planar members 39 are generally parallel to the outer extent of the holder 11.

Referring again to FIG. 15, recall that behind the rectangularly placed planar members 39 are the plurality of wedge shaped blind bores 37 and it is shown in FIG. 15 in dashed line format. The wedge shape of the plurality of blind bores 37 insures that the injection mold can withdraw in a direction normal to the planar portion 31 and out of the paper, toward the observer with respect to FIG. 6, but the existence of the plurality of blind bores 37 insures that each of the four rectangularly placed planar members 39 can ultimately flex to form a final friction or grabbing action at the extreme mouth of the series of square openings 35.

The shaped area within the series of square openings 35 should also ideally be ultimately tapered toward the abbreviated end 89 of the openings, else a more complicated mold with moving parts would be necessary to form such an internal shape existing between each square opening 35 and the abbreviated end 89.

FIG. 15 illustrates a "square on" view of one of the four rectangularly placed planar members 39. The illustration of the blind bore 37 in dashed line format to the rear emphasizes the wall-like characteristics of the structure in that having a space behind and in front admits to the possibility of some flexing. From the top of the rectangularly placed planar members 39, a short length of flat wall 141 is seen. From the short length flat wall 141, an angled transition 143 to the angled surface 85 is seen. The angled surface 85 extends outward, in the direction of the observer, along its length in a direction from the angled transition 143. The angled surface 85 extends forward at is maximum extent at the bottom of a "bib" shape. Below the angled surface 85 is the curve shaped wall 87. The curve shaped wall 87 extends outwardly from corners 145 somewhat cylindrically in the direction of the observer of FIG. 15. Note that the corners 145 extent to the top level of the angled surface 85 and the surfaces of the curved shaped wall are curved even near their uppermost extent where interrupted by the angled surface 85. Along the length of the curve shaped wall 87, it tapers in the direction of the observer of FIG. 15. Below the curve shaped wall 87, an inner wall 147 of the conical second portion 77 is seen, and which marks a transition to an inwardly curved wall shape.

Referring to FIG. 16, a view taken with regard to line 16-16 shows the side profile of the surfaces seen in FIG. 15 and illustrating the lateral extent of the associated surfaces seen at the same level as seen in FIG. 15. One of the corners 145 is seen in dashed line format. As can be seen, angled surface 85 assists in guiding a needle tip 63 of the hypodermic needle 51, while the curve shaped wall 87 forms a line of concentration of frictional forces on any rounded object, such as needle hub 53, along its center between the angled surface 85 and the inner wall 147. The square nature of the flat wall 141 and the angled surface 85 help engage the square nature of the hub 53 of the hypodermic needle 53. As such, a transition from square facilitated entry for square turning engagement transitions into a concentrated contact and friction surface interaction with the curve shaped wall 87. This combination of structures thus facilitates entry, rotational lock and axial frictional engagement.

Referring to FIG. 17, a variation of the hypodermic needle holder of the invention is seen as a hypodermic needle holder 151 which has many of the same structures seen for holder 11, including a lid portion 153. However, on lid portion 153, there is no latch 23 or catch 25. Rather the lid portion 153 is more closely contour matched to the shape of the opening 15. Lid portion 153 includes a raised projection 155 about a position just inside of the outer periphery of the lid portion 153, positioned to enter the opening 15 when the lid portion 153 is closed over the opening 15. The raised projection 155 may be made to form a more irreversible engagement and seal with respect to the opening 15 when the hypodermic needle holder 151 is closed. In the configuration shown, the outer surface of the raised projection may have a complementary shape matching the inner periphery of the opening 15 to form a snap shut seal. The snap shut mechanism, when combined with the matching peripheral shape, reduces the possibility that the hypodermic needle holder 151 will be inadvertently opened once it is closed.

As can be seen in FIG. 17, a reduced thickness portion 157 is located at the center of a hinge 159 between the lid portion 153 and the opening 15, to more exactly define the fold of the hinge 159 and to place the raised projection 155 exactly within the opening 15 for a more automatic alignment. Once the raised projection 155 engages the complementary matching surface 161 within the body portion 13 of the opening 15, a secure snap shut relationship will be had.

FIG. 17 also illustrates a pair of hook arms 165 and 167 extending from the body portion 13, but also from near the upper end of the tapered flanges 47, and may be thought of as an extension of the tapered flanges 47. This enables the hook arms 165 and 167 to garner additional structural strength from the body of the hypodermic needle holder 151. Hook arms 165 and 167 are also advantageous for enabling the body portion 13 to be hung from the side, as from a tray or cart or box or container, essentially any object which has a vertical wall. Where an object has a thick wall and is vertical, the body portion 13 is likely to hang more upright. On trays with thin walls and more inclined walls, the body portion 13 may hang at a more inclined angle. Any independent support which enables a practitioner to avoid having to support the body portion 13 by hand will significantly reduce incidence of needle stick.

Each of the hook arms 165 and 167 includes a lateral member 171 which extends generally parallel to the top of the body portion 13, and an opposing member 173 which extends opposite to the length of the tapered flange 47. The taper of the tapered flange 47 compared to the inside of the respective hook arm 165 and 167 causes the opening 15 to tilt somewhat away from any object from which it depends to make the opening 15 more easily available for manual manipulation of hypodermic syringes. The ability to utilize the hypodermic needle holder 151 by independently supporting it, further reduces the chances of a needle stick by removing the user's hand which is not engaging the syringe away from the vicinity of the hypodermic needle holder 151. It also frees the medical practitioner's other hand for other tasks, not to mention the fact that it frees up tray or table area for other items. Further, the opposing members 173 could be forced through other material such as a box or other paper or cardboard structure to instantly obtain stability from other weaker objects. As can also be seen, the angle and spacing of the opposing members 173 represents an angular spread which can further assist in affixing the hypodermic needle holder 151 to deformable surface by enabling a progressive tearing action or a pinching action.

Referring to FIG. 18, a further view of hypodermic needle holder 151 is seen. From the left, the side profile of the hook arm 167 is seen. Across the body portion 13, the thickness of the reduced thickness portion 157 is seen with respect to the center of hinge 159. A dashed arrow illustrates the radius of closure and is taken with respect to a pivot at the reduced thickness portion 157.

The side profile of the raised projection 155 is seen to have a laterally extending or laterally thickened projection 181 which is seen in profile as extending generally toward and away from the body portion 13. In practice, the laterally thickened projection 181 may extend completely about the raised projection 155, or only partially. A partial extension may, for example, only exist along the side of the raised projection 155 on one of the elongated linear lengths of the raised projection 155, or two. Or the partial extension may, for example, only exist along the curved sides of the raised projection 155. Much may depend upon the strength of closure. In addition, the projection may be angled to provide one way, very irreversible closure. In any event, re-opening for purposes of unusual circumstance may still be had with the configuration shown by placing a prying tool into the crack between the body portion 13 and the lid portion 153.

At the bottom of the hypodermic needle holder 151, a tear away strip 185 covers a layer of adhesive 187. Adhesive layer 187 can be located elsewhere, as is shown in FIG. 18, including on one side of the hypodermic needle holder 151 or the other and whether or not on the flanges 47.

Whether or not there is an available structure with which to engage one or more of the hook arms 165 and 167, the hypodermic needle holder 151 can be supported by adhesion to any suitable surface. Where the hypodermic needle holder 151 is made of a polymeric substance, the adhesive layer 187 will have high affinity for the bottom surface of the hypodermic needle holder 151 and provide a clean adhesive support for the hypodermic needle holder 151 on any stable surface. After use, and after closure, the hypodermic needle holder 151 can be manually and forcibly tipped to one side to disengage it cleanly from any surface. Further, the hypodermic needle holder 151 may be supplied with an accompanying area of plastic base such as a credit card thickness of plastic to use as a further support, especially where there is no clean surface immediately employable for such purpose. Such a support might have an area equivalent to the area of two or three wallet sized credit cards and may be pre-packaged with the hypodermic needle holder 151 as either a package add in or co-molded structure. Where such a base is utilized, the base can be removed and discarded after the hypodermic needle holder 151 use has terminated and after the lid portion 153 is closed over the opening 15.

The adhesive layer 187, and hook arms 165 and 167 are but two types of structures for additional support of the hypodermic needle holder 151, and other structures can be employed. Additional support assists medical practitioners by eliminating the chances and the necessity to bring the practitioner's hands together which has a higher likelihood where the hypodermic needle holder 151 is manually held. Even where manual holding is necessary, manual grasping can occur at the bottom end of the holder 151, away from the opening 15.

Figure 19:
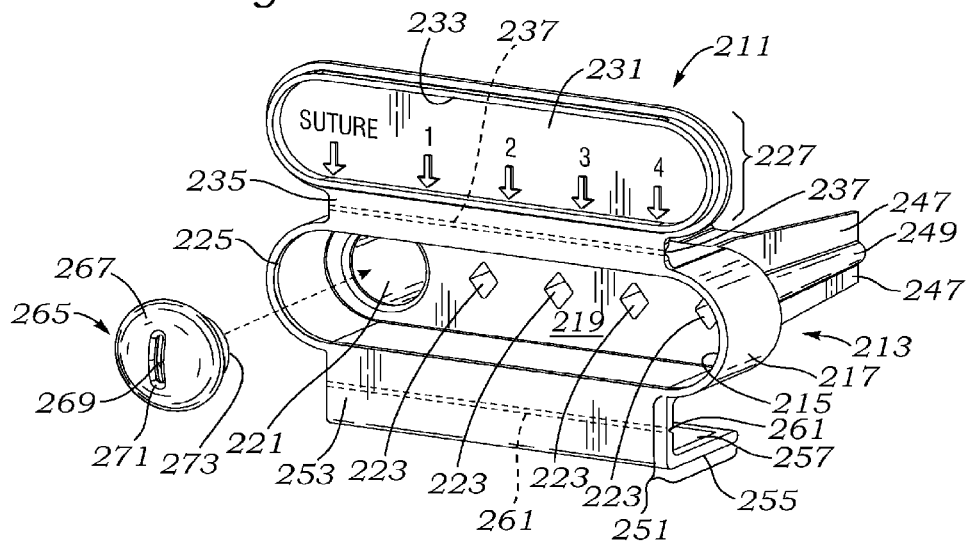
FIG. 19 is a perspective view of a second embodiment of hypodermic needle holder of the present invention, and illustrates view looking into a large opening which opens access to a suture opening and a series square or diamond openings, with the suture opening having a suture cap shown in exploded view.
Figure 20:
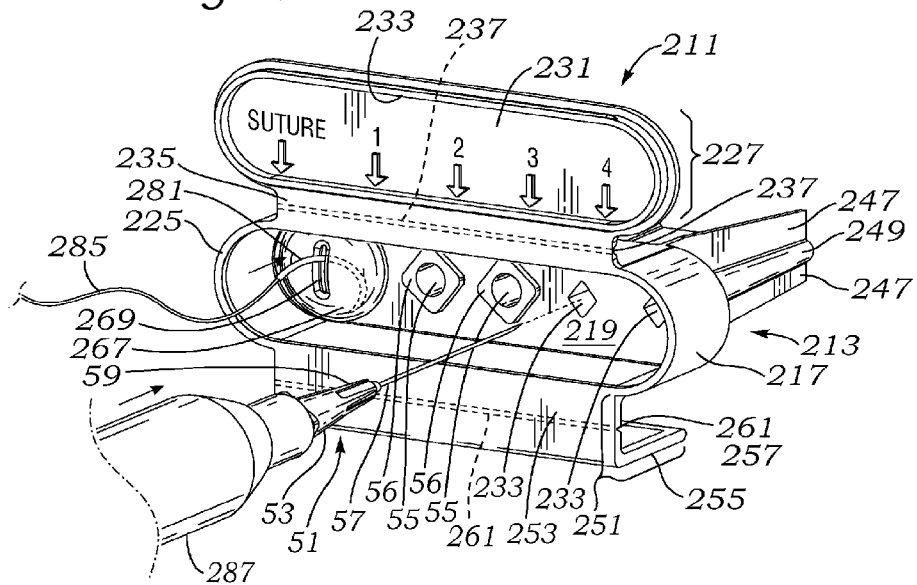
FIG. 20 is a perspective view of the second embodiment of hypodermic needle holder of the present invention seen in FIG. 19, and illustrates attachment of the suture cap over the suture opening and a suture in a position of partial entry through the slot opening of the suture cap and into the sutures opening as well as an approach of a hypodermic needle into receptacle number 3 with receptacles number 1 and 2 being occupied and receptacle number 4 being vacant.

Referring to FIG. 19, a perspective view of a second embodiment of the invention is seen as a hypodermic needle holder 211 which, similar to holder 11, has a body portion 213 having an opening 215. Within opening 215 is a continuous wall 217 which projects away from a planar portion 219. Within the planar portion 219 is located a larger circular opening which is configured as a suture opening 221. To the right of suture opening 221 is seen a series of four hypodermic needle retaining openings 223. The continuous wall 217 provides a space to accommodate the length of the needle hub 53 after engagement of the hypodermic needle 51 with the hypodermic needle retaining openings 223.

Two main structures may be continuous with and depend from an upper rim 225 of the wall 217. Projecting in one direction is a lid closure 227 which includes a planar portion 231 having a projecting rim 233. The projecting rim 233 forms a snap engagement with the opening 215 adjacent the upper rim 225. A web member 235 joins the lid closure 227 and the continuous wall 217. Web member 235 may have a hinge stabilization groove 237 to control the line of bending between the lid closure 227 and the rim 225 and wall 217. Control of the angle of the lid closure 227, and the extent to which projecting rim 233 projects with respect to includes a planar portion 231 can insure a positive, secure snap closure.

Also shown on the planar portion 231 are raised and impressed signage labeled "SUTURE", "1", "2", "3", and "4" to enable a user to more readily identify the function of the suture opening 221 and to keep up with which of the four hypodermic needle retaining openings 223 has been used and for what service. A pair of tapered flanges 247 are seen to either side of an external curved shape resulting from an accommodation of the endmost one of the four hypodermic needle retaining openings 223.

The other one of the two main structures and which is continuous with and depend from an upper rim 225 of the wall 217, is a support flange 251 which can be made of any shape. However as seen in the drawings, a flange having an "L" shaped cross section is shown, and includes a first planar member 253 extending generally level with the top of upper rim 225, and a second planar member 255 which is angled with respect to the first planar member 253. An optional adhesive release strip 257 is shown which may be affixed at various locations about either the flange 251, and is shown in FIG. 19 as overlying a thin layer of adhesive on the inside of the second planar member 255 facing the body portion 213. The thin adhesive underlying adhesive release strip 257 facilitates attachment of the hypodermic needle holder 211 in a stable position in a variety of situations where the structure available to hold the hypodermic needle holder 211 is narrower than the lateral space between the support flange 251 and the body portion 213.

In addition, the first planar member 253 is shown as having a groove 261 which may provide some flexibility in positioning the hypodermic needle holder 211 whether or not the inside of the second planar member 255 is adhesively attached to some other structure. The groove 261 enables a stable living hinge to be formed along a line in the first planar member 253. Where second planar member 255 is adhesively attached to some other structure, it enables the body portion 213 to be angularly adjusted to assume the angle desired, especially as supported by another structure to achieve the exact position desired. Further, where a horizontal surface is available for attachment of an adhesive layer, such as may exist on one side of the second planar member 255, the groove 261 permits the second planar member 255 and half of the first planar member 253 to be flipped up with respect to the first planar member 253 to complete attachment. Further, an adhesive layer and an adhesive release strip 257 may be provided elsewhere, including the continuous wall 217, or on the underside of the first planar member 253. A multiplicity of adhesive layers and corresponding adhesive release strips 257 may be located in advantageous positions on the hypodermic needle holder 211 as may be exposed by the user as needed.

To the left of the body portion 213 and shown exploded from a position covering the suture opening 221 is a suture cap 265. Although the hypodermic needle holder 211 is expected to be available with the suture cap 265 in place, it is possible that it may be provided separately and for user insertion, or it can be provided covering the suture opening 221 such that it can be removed if desired. Suture cap 265 is shown as having curved outward surface 267 and a slot 269 at the center. The slot entrance may have curved edges 271 at the opening 269. The suture cap 265 has a rearward engagement projection 273 which fits partially into the suture opening 221 to help secure the suture cap 265 into and over the suture opening 221.

Referring to FIG. 21, a plan view looking into the main opening 215 illustrate illustrates the hypodermic needle holder 211 with the suture cap 265 in place, and illustrates a suture needle 281 with attached suture 285 being placed through the opening 269. The hooking action of the suture needle will easily allow it to deliberately enter the opening 269 where it will be retained within the suture opening for later disposal. It is preferable for the suture cap 265 to be preferably permanently attachable over the suture opening 221 as the space covered by the suture cap 265 is expected to be accessed for disposal rather than removal.

To the right of the suture 285 and suture needle 281, a pair of hypodermic needles 51 are seen at two of the four hypodermic needle retaining openings 223, as inserted and retained position at positions "1 and 2". A syringe 287 with hypodermic needle 51 is shown approaching position "3" of the four hypodermic needle retaining openings 223. The rectangular opening of the four hypodermic needle retaining openings engages ribs 59 of the needle hub 53 to both frictionally engage needle hub 53 and to enable syringe 287 to be turned to facilitate the lock and unlock the hypodermic needle 51 from the syringe 287.

Referring to FIG. 21, a plan view looking into the main opening 215 illustrates the spacing of the suture opening 221 and four hypodermic needle retaining openings 223 across the planar portion 219. Within each of the four hypodermic needle retaining openings 223 a transition from rectangular or diamond to circular profile of a tapered conical needle retaining space 291 is seen.

Referring to FIG. 22 is a perspective sectional view taken along line 22-22 of FIG. 21 and illustrating the rectangular to tubular transition from the diamond or rectangular shaped needle retaining openings 223 to the tapered conical needle retaining space 291. Portions of the body between the tapered conical needle retaining spaces 291 are shown are web portions 293 of the body portion 213. Further details of the fit of the suture cap 265 into the suture opening 221 are also observed, and an exterior wall 295 bounding the interior space of the suture opening 221 is seen.

Referring to FIG. 23, a sectional view taken along line 23-23 of FIG. 21 illustrates the rectangular or diamond to tubular transition from four hypodermic needle retaining openings 223 to tapered conical needle retaining spaces 291 is such that the tapered conical needle retaining spaces 291 is only necessary to be long enough for the needle shaft 57. Also shown are alternative sites for adhesive release strips 257 including onto the continuous wall 217 on each side of the body portion 213, the underside of first planar member 253 and the inward facing side of second planar member 255. The more adhesive release strips are provided on the hypodermic needle holder 211, the more easily a user can create attachments to a variety of structures which may be able for use by the medical practitioner.

Figure 24:
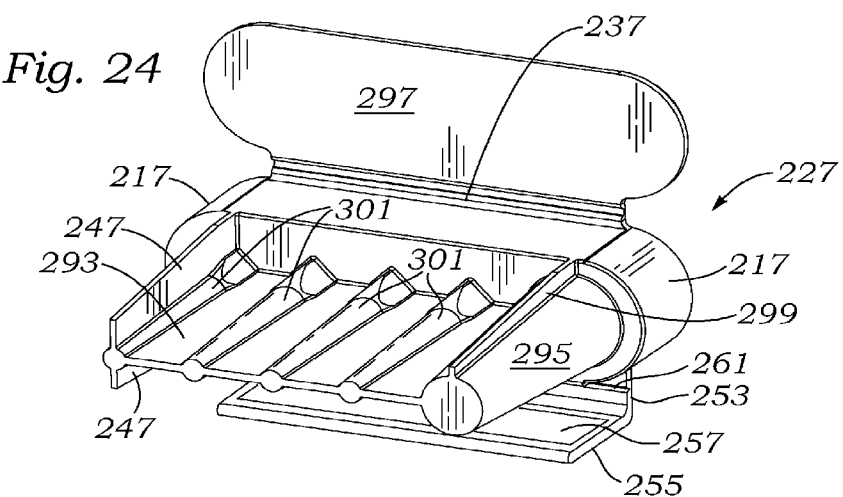
FIG. 24 is a perspective view from the underside and illustrating the flange nature of the structure and giving a view of the reverse underside of the flange and lid.

Referring to FIG. 24, a perspective view from the underside illustrates the flange nature of the structure of the hypodermic needle holder 211 and gives a view of the reverse underside of the web portions 293 of the body portion 213 and the top side of the lid closure 227. Note that there are no deliberate handles or releases seen on the top side 297 of the lid 227 which would encourage a re-opening of the hypodermic needle holder 211. This is because the use of the hypodermic needle holder 211 is intended to normally end when the lid closure 227 is snapped shut. Also seen is an abbreviated width flange 299 adjacent exterior wall 295. A series of exterior walls 301 of the four hypodermic needle retaining openings 223 and tapered conical needle retaining spaces 291 are also seen.

Figure 25:
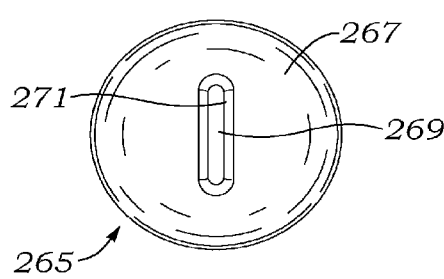
FIG. 25 is a front plan view of the suture cap.
Figure 26:
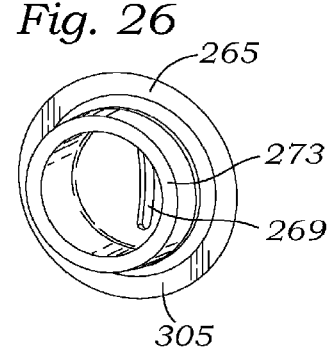
FIG. 26 is an underside perspective view of the suture cap showing the engagement projection and the reverse side of the suture entry slot.
Figure 27:
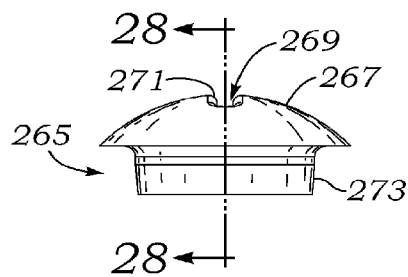
FIG. 27 is a side plan view of the suture enclosure cap.
Figure 28:
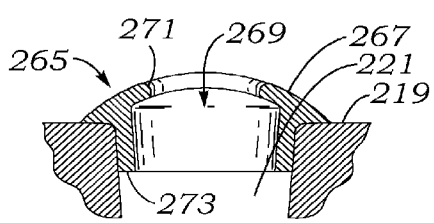
FIG. 28 is a section taken along line 28-28 of FIG. 27.

Referring to FIG. 25, a front plan view of the suture cap 265 is seen and illustrating more prominently the curved edges 271 of the slot 269. Referring to 26 an expanded underside perspective view of the suture cap showing the engagement projection 273 and the reverse side of the suture entry slot 269. A flat annular underside 305 for mating against the planar portion 219 of the body portion 213 is also seen. Referring to FIG. 27, a side plan view of the suture enclosure cap 265 is seen and shows the profile of the curvature of the curved outward surface 267, the slot 269 and its curved edges 271. Referring to FIG. 28, a section taken along line 28-28 of FIG. 27 is shown with the suture enclosure cap 265 in position over the suture opening 221 of the body portion 213.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed is:

1. A hypodermic needle holder for safely storing and disposing of a hypodermic needle, and comprising:
    a body portion and a lid portion connected to said body portion said body portion having a main opening lockably coverable by said lid portion;
    at least a plurality of needle retaining openings, each of the needle retaining openings associated with and in communication with an isolated chamber, each needle retaining opening in communication with said main opening for frictionally engaging and retaining a hypodermic needle by at least frictional engagement upon insertion of a hypodermic needle within an associated one of the plurality of said plurality of needle retaining openings;
    support structure, including a flange having a first planar member connected to and extending away from said body portion, and a second planar member attached to said first planar member at an angle for enabling a hypodermic needle holder to be stably supported and utilized for engaging and retaining a hypodermic needle without manual grasping of either one of the hypodermic needle and said hypodermic needle holder and further comprising at least one container in communication with said main opening for the disposal of miscellaneous dangerous material and wherein a cap having an entry slot covers said at least one container.

2. The hypodermic needle holder as recited in claim 1 and wherein said lid portion is pivotably moveable between a first, open position and a second, closed locked position wherein said opening of said main body portion is fixably enclosed by said lid portion.

3. The hypodermic needle holder as recited in claim 2 and wherein said lid portion further includes a raised projection for engaging and fitting within said main opening for securing said lid portion in a closed position for retention of contents of said hypodermic needle holder.

4. The hypodermic needle holder as recited in claim 2 and wherein each said isolated chamber is accessible only through its associated one of said at least a plurality of needle retaining openings.

5. The hypodermic needle holder as recited in claim 1 and further comprising at least one container in communication with said main opening for the disposal of miscellaneous dangerous material.

6. The hypodermic needle holder as recited in claim 5 and wherein said at least one container is frustoconical.

7. The hypodermic needle holder as recited in claim 1 wherein said entry slot includes curved edges to facilitate the entry and retention of a suture needle and suture.

8. The hypodermic needle holder as recited in claim 1 and wherein said support structure further comprises a layer of adhesive attached to at least one of said body portion, said first planar member and said second planar member of said hypodermic needle holder for enhancing the upright stability of said hypodermic needle holder.

9. The hypodermic needle holder as recited in claim 1 and wherein said lid portion is connected to said body portion opposite attachment of said first planar member first end connection to said body portion.

10. A hypodermic needle holder for safely storing and disposing of a hypodermic needle, and comprising:
    a body portion and a lid portion connected to said body portion said body portion having a main opening lockably coverable by said lid portion;
    at least a plurality of needle retaining openings, each of the needle retaining openings associated with and in communication with an isolated chamber, each needle retaining opening in communication with said main opening for frictionally engaging and retaining a hypodermic needle by at least frictional engagement upon insertion of a hypodermic needle within an associated one of the plurality of said plurality of needle retaining openings;
    support structure, including a flange having a first planar member connected to and extending away from said body portion, and a second planar member attached to said first planar member at an angle for enabling a hypodermic needle holder to be stably supported and utilized for engaging and retaining a hypodermic needle without manual grasping of either one of the hypodermic needle and said hypodermic needle holder and further comprising a groove in said first planar member of said flange to permit angular movement of said body portion with respect to said first planar member.

11. The hypodermic needle holder as recited in claim 10 and wherein said support structure further comprises a layer of adhesive attached to at least one of said first and said second planar members for enhancing the upright stability of said hypodermic needle holder.

12. The hypodermic needle holder as recited in claim 11 and wherein said hypodermic needle holder is fabricated from a polymeric, at least slightly resilient material.

13. The hypodermic needle holder as recited in claim 12 and wherein said polymeric, slightly resilient material is plastic.

14. A hypodermic needle holder for safely storing and disposing of a hypodermic needle, and comprising:
- a body portion and a lid portion connected to said body portion and a main opening lockably coverable by said lid portion;
- at least a plurality of needle retaining openings, each needle retaining opening associated with and in communication with an isolated chamber, each of said plurality of needle retaining openings in communication with said main opening for frictionally engaging and retaining a hypodermic needle by at least frictional engagement upon insertion of a hypodermic needle within said needle retaining opening;
- at least one container in communication with said main opening for the disposal of miscellaneous dangerous material; and
- a cap having an entry slot attached over said at least one container.

15. The hypodermic needle holder as recited in claim 14 and wherein said cap includes an annular shaped engagement projection for fitting at least partially within said at least one container and a curved outward surface which is wider than said annular shaped engagement projection.

16. The hypodermic needle holder as recited in claim 15 and wherein said entry slot is located within said curved outward surface.

17. The hypodermic needle holder as recited in claim 14 and wherein said entry slot of said cap has curved edges.

18. The hypodermic needle holder as recited in claim 14 and wherein said lid portion is pivotably moveable between a first, open position and a second, closed locked position wherein said opening of said main body portion is fixably enclosed by said lid portion.

19. The hypodermic needle holder as recited in claim 14 and wherein said lid portion further includes a raised projection for engaging and fitting within said main opening for securing said lid portion in a closed position for retention of contents of said hypodermic needle holder.

20. The hypodermic needle holder as recited in claim 14 and further comprising a layer of adhesive attached to said body portion for enhancing the upright stability of said hypodermic needle holder.

\* \* \* \* \*